US010964150B2

(12) United States Patent
Schmidt et al.

(10) Patent No.: US 10,964,150 B2
(45) Date of Patent: Mar. 30, 2021

(54) DEVICE FOR PROCESSING VALUABLE DOCUMENTS AND METHOD FOR OPERATING THE DEVICE

(75) Inventors: Alfred Schmidt, Munich (DE); Peter Dopfer, Geltendorf (DE); Erwin Demmeler, Memmingen (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 2171 days.

(21) Appl. No.: 13/055,499

(22) PCT Filed: Aug. 5, 2009

(86) PCT No.: PCT/EP2009/005672

§ 371 (c)(1), (2), (4) Date: Jan. 24, 2011

(87) PCT Pub. No.: WO2010/015395

PCT Pub. Date: Feb. 11, 2010

(65) Prior Publication Data

US 2011/0120015 A1 May 26, 2011

(30) Foreign Application Priority Data

Aug. 6, 2008 (DE) ..................... 10 2008 036 599.8

(51) Int. Cl.

*G07D 11/10* (2019.01)
*G07D 11/26* (2019.01)
(Continued)

(52) U.S. Cl.

CPC ............. *G07D 11/10* (2019.01); *G07D 11/14* (2019.01); *G07D 11/235* (2019.01);
(Continued)

(58) Field of Classification Search

CPC ...... G07D 11/10; G07D 11/235; G07D 11/14; G07D 11/26; G07D 11/237; G07D 11/60
(Continued)

(56) References Cited

U.S. PATENT DOCUMENTS 4,227,074 A 10/1980 Tuyoshi
4,510,381 A 4/1985 Fukatsu
(Continued)

FOREIGN PATENT DOCUMENTS

DE 4303866 8/1994
DE 19645652 5/1998
(Continued)

OTHER PUBLICATIONS

English Translation of JP2004020804A.*
(Continued)

*Primary Examiner* — Jeffrey A Shapiro
(74) *Attorney, Agent, or Firm* — Bacon & Thomas, PLLC

(57) ABSTRACT

The invention relates to an apparatus (1) for processing documents of value, in particular bank notes, and a method for operating such an apparatus (1). The apparatus (1) includes several processing zones (2, 3, 4, 5, 11, 12, 13), such as for example an input module (2), an operating module (3) and an output module (4). The apparatus (1) is further set up to detect events in the processing zones (2, 3, 4, 5, 11, 12, 13), which require an intervention of an operator. The processing zones (2, 3, 4, 5, 11, 12, 13) each have at least one cover (6), which, dependent on such a detected event, is automatically opened without intervention of the operator.

20 Claims, 2 Drawing Sheets

(51) Int. Cl.
*G07D 11/237* (2019.01)
*G07D 11/14* (2019.01)
*G07D 11/235* (2019.01)
*G07D 11/60* (2019.01)

(52) U.S. Cl.
CPC ........... *G07D 11/237* (2019.01); *G07D 11/26* (2019.01); *G07D 11/60* (2019.01)

(58) Field of Classification Search
USPC ........... 194/206, 207; 209/534; 399/21, 110, 399/124, 125
See application file for complete search history.

(56) References Cited

U.S. PATENT DOCUMENTS

| | | | | |
|---|---|---|---|---|
| 4,533,135 | A | 8/1985 | Barker | |
| 4,811,680 | A * | 3/1989 | Genth | 114/201 R |
| 5,404,840 | A | 4/1995 | Wiedenmann et al. | |
| 2003/0015395 | A1* | 1/2003 | Hallowell et al. | 194/206 |
| 2007/0019375 | A1* | 1/2007 | Ligtenberg | G06F 1/1616 361/679.26 |
| 2007/0267808 | A1* | 11/2007 | Cha et al. | 271/273 |
| 2009/0043172 | A1* | 2/2009 | Zagorchev | A61B 6/032 600/300 |
| 2009/0159585 | A1* | 6/2009 | Bally et al. | 219/390 |
| 2009/0272795 | A1 | 11/2009 | Stapfer et al. | |
| 2009/0293424 | A1* | 12/2009 | Mori | 53/167 |

FOREIGN PATENT DOCUMENTS

| | | | | |
|---|---|---|---|---|
| DE | 102006028633 | | 12/2007 | |
| JP | 404350044 | A * | 12/1992 | 271/273 |
| JP | 2004020804 | A * | 1/2004 | G03B 27/62 |
| WO | 0017828 | | 3/2000 | |
| WO | WO0162650 | A1 * | 8/2001 | G07D 9/00 |

OTHER PUBLICATIONS

English Translation of JP404350044A.*

International Search Report in PCT/EP2009/005672, dated Jan. 29, 2010.

Search Report of German PTO regarding German Patent Application No. 102008036699.8, dated Aug. 13, 2009.

* cited by examiner

DEVICE FOR PROCESSING VALUABLE DOCUMENTS AND METHOD FOR OPERATING THE DEVICE

BACKGROUND

1. Field

The present invention relates to an apparatus for processing documents of value and a method for operating the apparatus, in particular for eliminating a malfunction at the apparatus.

2. Related Art

Apparatuses for processing documents of value, such as bank note processing machines, usually consist of several modules or processing zones, which are disposed in succession and carry out different processing steps. The number, type and arrangement of the modules may vary depending on the requirements on the processing of the documents of value. A bank note processing machine typically comprises at least one input module, one operating module and one or more output modules. After the input, the bank notes are singled in the input module and on a measuring path sensed by sensors, so as to recognize bank notes unfit for circulation. These are separated from the bank notes fit for circulation and separately outputted or, where necessary, destroyed. The bank notes fit for circulation are transported further and in the output module, for example, outputted in bundles. Optionally, such an apparatus can have a separate larger output module for handling larger amounts of bank notes, a shredder module for destroying selected bank notes and/or modules for stacking or bundling processed bank notes. The sequence of the bank note processing can be controlled and monitored by the operator via an operator interface which is usually located in the operating module. The modules can partly be connected to each other by coupling modules and/or drive modules.

If there occurs an event which requires an operator to intervene in the work process, this is detected by suitable sensors and displayed on the display of the operating module. This can be the case, for example, when there occurs a bank note jam, or consumables must be renewed. The operator reads the information about the malfunction from the display and opens a cover of the bank note processing machine, which cover is associated to the corresponding processing zone, for example a lifting door or flap, so as to be able to access the interior of the machine and to eliminate the malfunction. After the malfunction has been eliminated and the opened module has been closed, the machine is restarted and the work process can be continued. In particular with bank note processing machines having many different modules, accurate information about the location of the malfunction is necessary, so that the operator can intervene at the right place and opens the right module.

SUMMARY OF THE DISCLOSURE

It is the object of the present invention to optimize the work processes at an apparatus for processing documents of value.

This object is achieved according to the invention by an apparatus and a method according to the independent claims. Advantageous developments and embodiments are stated in the claims dependent thereon.

According to the invention it is now provided that when there is detected an event which requires an, in particular manual, intervention of the operator, a cover of the relevant processing zone, which cover is associated to the detected event, is automatically opened without intervention of the operator. The cover associated to the event is in particular the cover of that processing zone in which the operator must perform the intervention. One or more covers of one or more processing zones can be automatically opened, here.

Thus, the operator does no longer have to determine the location, i.e. the processing zone in which the event has occurred, and find the associated cover, on the basis of information displayed on a display. By the right cover opening automatically, the operator is led directly to the processing zone in which an intervention of the operator is required. With the apparatus according to the invention, the operator is thus led immediately to the right module. In addition, this relieves the operator, since he does not have to expend any energy to open the often large and heavy cover, i.e. the ergonomics of operation is also improved.

For the safety of the operator, the bank note processing in the bank note processing machine is stopped before or at the latest as soon as a cover of the bank note processing machine is automatically opened. Only when all covers are closed, the operation of the machine can be continued. An exception is a service mode during which the machine continues to run, for example for maintenance purposes, despite opened covers.

To increase the safety of persons, in particular of the operator or further persons who stay in the vicinity of the bank note processing machine and who might be surprised by the unexpected opening of the cover, the bank note processing machine can indicate the automatic opening of the cover by one or more additional signals. The indication of the additional signals can be started shortly before the automatic opening or simultaneously with the automatic opening of the cover. For example, as additional signals there are used acoustic and/or visual signals which are displayed on the display of the operating module and/or on the module of the cover to be opened and/or on the cover itself.

Furthermore, there can be optionally provided that the automatic opening of the cover associated to the detected event is effected only after an opening confirmation by the operator of the bank note processing machine. In this way, any risks to the operator or further persons can be excluded. For this, for example, on the display of the operating module is displayed a message which informs the operator that at least one of the covers will be opened automatically and prompts the operator to make an opening confirmation. The confirmation of the opening can be effected e.g. by pressing a button or by touch screen input at the operating module. Moreover, the message may also inform about which one of the covers will be opened automatically, so that the operator is informed early about the location of the intervention. As soon as the bank note processing machine receives the opening confirmation of the operator, the one or more covers associated to the detected event are opened automatically.

The automatic opening of the covers can be provided within the framework of one or more operation modes of the bank note processing machine, while in other operation modes an automatic opening of the covers is not effected. For example, the bank note processing machine is configured such that the operator can freely choose, whether the covers are to be opened automatically upon one or more certain events, and upon which events this is to be effected.

The automatic opening of the covers can also be deactivated by the operator, if required, for all events.

Preferably, the automatic opening of the covers is effected by means of at least one actuator per cover, e.g. an actuating cylinder, which acts upon the respective cover. The actuating cylinder can be for example a pneumatic cylinder which pneumatically controls the opening movement. The necessary compressed air can be provided for example via an additional module and can reach via a corresponding pipe system the pneumatic cylinder, whose position is controlled through valves. Upon the detection of an event in the apparatus, one of the valves connected with the pneumatic cylinder of the associated cover is opened, so that through the pressure build-up the cover is opened. Instead of the pneumatic control there can also be provided a hydraulic control or an electric, or electric-motor drive of the cover.

To support the opening movement of the covers there can be provided, in addition to the actuating cylinder, at least one gas pressure spring per cover. The gas pressure spring also serves to hold the respective cover in the fully opened position, so that there is not required for example a pneumatic pressure to hold open the cover. With the gas pressure springs it is ensured that the covers remain open upon a pressure failure.

The closing of the covers is preferably started by the operator, by him activating a switch, for example a button, which is disposed at the opened module or centrally at the apparatus, for example at the operating module. Preferably, at the operating module, in particular at the display of the operating module, there is provided a central switch, by the one-time activating of which the operator can obtain the closing of all opened covers. In addition to the central switch, also at the modules themselves there are present switches for closing the respective covers. The closing can also be initiated, however, by a short pull on the respective cover. A possibly required opening of a cover, which is not triggered automatically, can be triggered in the apparatus according to the invention by the operator also giving it a short pull. The complete opening is then effected, as with the automatic opening, by the force generated by the actuator.

Moreover, it can be provided that upon the presence of a certain event the covers of the machine are automatically closed. The certain event can be e.g. the end of an intervention of the operator or the continuation of the bank note processing, for example when the transport system is switched on by the operator. The covers of the machine can also be closed automatically, as soon as the machine has detected a certain event which was triggered by the intervention of the operator, e.g. after sensors have detected that a malfunction has been eliminated successfully by the operator or that sufficient consumables are available again.

Preferably, the apparatus in addition has sensors that are set up to detect the fully opened and fully closed position of the covers. The end positions of the movement of the covers, for example, can have been adjusted before on the basis of the mechanical radius of movement. By means of the sensors there can also be recognized, for example, whether the covers are completely closed and the operation of the machine can be continued safely.

An advantageous embodiment of the invention comprises a pneumatic cylinder which is controlled by two valves with which compressed air can be applied to one end of the pneumatic cylinder in each case. By temporarily, at least partly closing one of the valves, the closing movement of the opened cover can be slowed down. Since the apparatus has processing zones of different sizes, in the case of particularly large and heavy covers for example the mid-open position is detected by an additional, adjustable transmitter on the pneumatic cylinder. By the temporary, at least partial closing of the valve, for a short time the pressure in the actuating cylinder is increased, so that the cover is caught and with the help of the gas pressure spring can close in a slowed-down movement. The partial closing can be effected by throttling in the compressed air pipe or by admitting a counterpressure to the pneumatic cylinder, for example by opening the other valve. With smaller and lighter covers the pressure of the gas pressure spring is sufficient for catching the weight.

An advantageous embodiment of the invention comprises a permanent activation of the actuator even in the closed state of the cover, e.g. the pressure in the actuating cylinder being permanently maintained upon closed cover. The covers here are pressed with a defined force tightly against the surrounding casing of the machine. As a result, vibrations or rattling noises are prevented and the noise insulation of the machine is improved.

DESCRIPTION OF THE DRAWINGS

The invention is described in the following with reference to the accompanying Figures, by way of example on the basis of an embodiment, in which.

DETAILED DESCRIPTION OF PREFERRED EMBODIMENTS OF THE INVENTION

Figure 1:
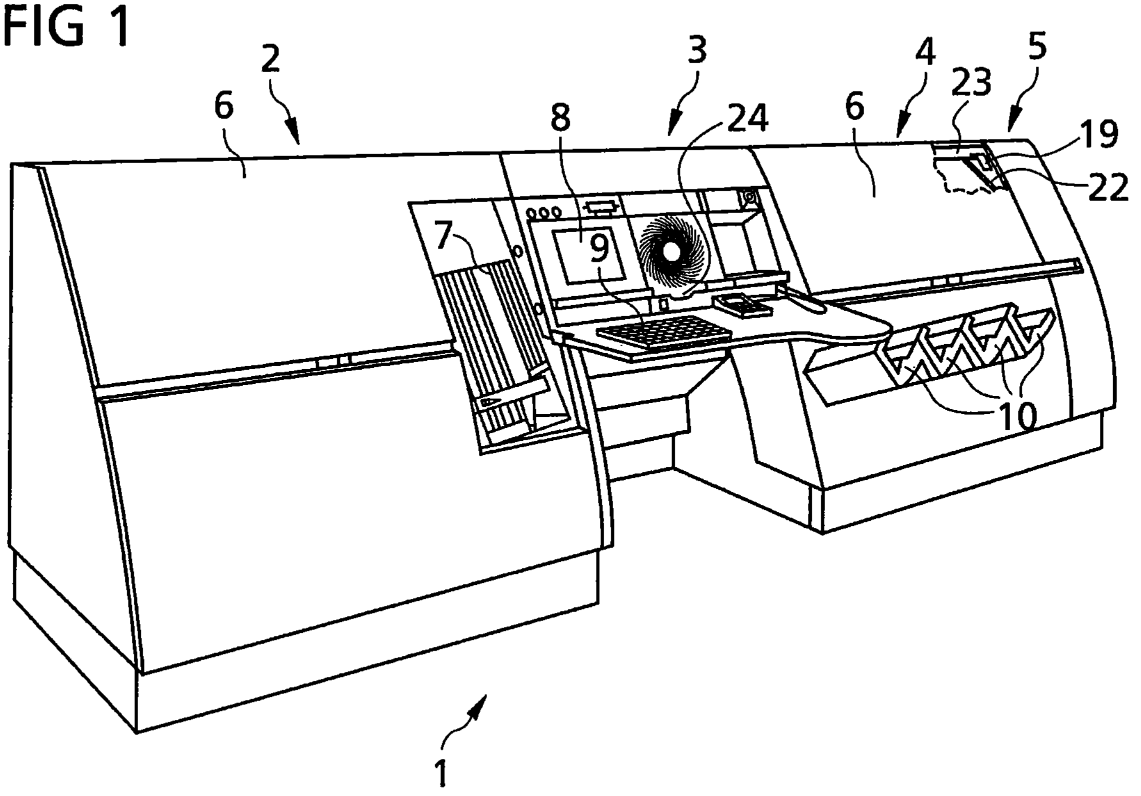
FIG. 1 shows a general view of a bank note processing machine in a perspective view.

In FIG. 1 there is represented a bank note processing machine 1, which is composed of many different processing zones, which are realized by modules 2, 3, 4, 5. The bank note processing machine 1 consists of an input module 2, an operating module 3, an output module 4 and a shredder module 5.

Bank notes which are to be processed by the bank note processing machine 1 are inserted by an operator into the input module 2 disposed on the left beside the operating module 3. For this, the input module 2 comprises an input pocket 7 which receives a stack of bank notes. After the input, the bank notes are singled by means of a singler, and checked by a measuring system in the form of a measuring path having checking sensors for example as to authenticity and/or as to their denomination and/or as to their fitness for circulation.

The input module 2 is followed by the operating module 3 which has a user interface with screen 8 and function keys 9 for operating the bank note processing machine 1 through an operator. Moreover, in the operating module 3 there is accommodated a reject pocket 24, where bank notes are stacked which were rejected on the basis of the measurements in the input module 2, for example bank notes recognized to be forgeries or bank notes which could not be unequivocally identified by the checking sensors in the input module 2. The bank notes from the reject pocket 24 are then subjected to a manual check and, if appropriate, again inserted into the input module 2. The other bank notes are further transported along a transport path in the bank note processing machine 1 to the output module 4.

The output of the bank notes checked and deemed to be fit for circulation in the output module 4 is effected in a bundled or stacked form. For this, the output module 4 has several stackers, strapping devices and bank note output pockets 10. A bank note processing machine 1 can have several different output modules 4, depending on the volume to be processed, so as to be able to process larger quantities of bank notes and output them together.

In the following shredder module 5, bank notes recognized to be unfit for circulation, for example damaged or heavily soiled bank notes, can be destroyed and then outputted into a secured pocket for disposal. The bank note processing machine 1 can further have a revision stacker for stacking bank notes unfit for circulation which are not to be destroyed. Optionally, there can also be connected to the bank note processing machine 1 a bundling device in which bank notes are bundled in certain quantities and wrapped with plastic foil.

Figure 2:
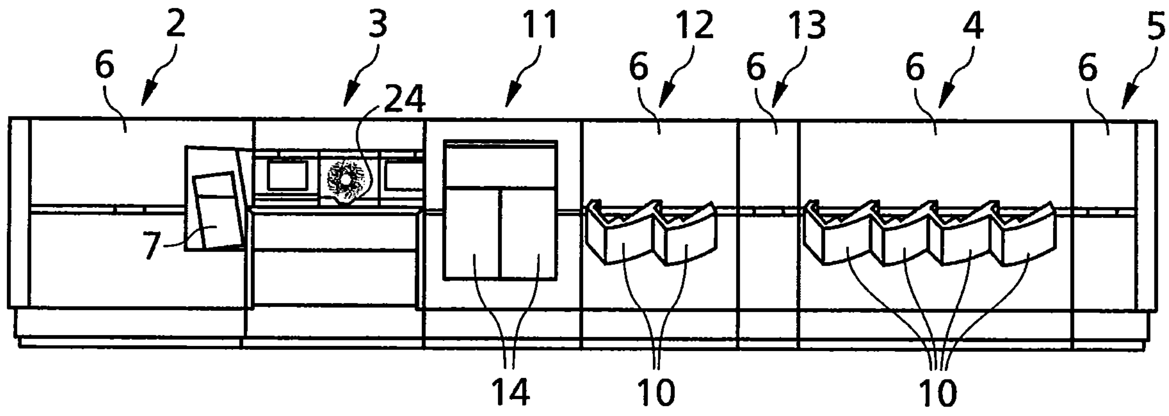
FIG. 2 shows a general view of a bank note processing machine with further modules in a front view.

In FIG. 2 there is shown the structure of a bank note processing machine, which besides the input module 2, the operating module 3, the output module 4 and the shredder module 5, has additional modules.

Two additional output modules 11, 12 increase the output volume of the bank note processing machine. The large output module 11 for outputting has two output stackers 14 without strapping device, into which larger quantities of bank notes can be outputted in a loosely stacked manner. The output module 12 is basically built-up like the output module 4, but has only two bank note output pockets 10, into which bank notes can be outputted in a bundled manner. In addition, this more complex bank note processing machine comprises a coupling module 13 which connects the output modules 12 and 4 to each other. This can also be formed as a drive module, in order to improve the transport of the bank notes to be processed along the long transport path. The modules of the bank note processing machine 1, in particular the input module 3, the shredder module 5, the coupling module 13 and the output modules 4, 11, 12 are closed by covers 6 which can be formed as lifting doors.

For supplying the bank note processing machine 1, an internal or external air supply module can be provided, which provides, if needed, compressed air and, if necessary, negative pressure. This air supply module supplies e.g. pneumatic cylinders with compressed air, which according to the invention are provided for automatically opening the covers 6.

The covers 6, which cover the respective modules of the bank note processing machine 1, are formed to automatically open themselves in case of a malfunction whose elimination requires an intervention of the operator, such as for example in case of a bank note jam, or in case of malfunctions of the strapping device or bundling device. There may also be other events which require an intervention of the operator. The covers 6 can also be automatically opened when consumables are to be refilled or replaced, or when light barriers or the checking sensors for evaluating the bank notes along the measurement path are to be checked and/or cleaned. Thus, such events can be manifold, so that here the concrete representation of the sensors, with which the respective events are detected, is omitted. The sensors are monitored by a control unit, which prompts the opening of the cover 6 associated to the respective sensor, as soon as the sensor detects a malfunction. Upon all these events, the bank note processing machine 1 is stopped by the control unit, so that the safety of operators is not endangered.

The covers 6 are manually movable when the bank note processing machine 1 is switched off. This is expedient for example upon manual interventions, which cannot be carried out with a switched-on bank note processing machine 1. Also under safety aspects it is important that all covers 6 can be manually activated by the operator.

Figure 3:
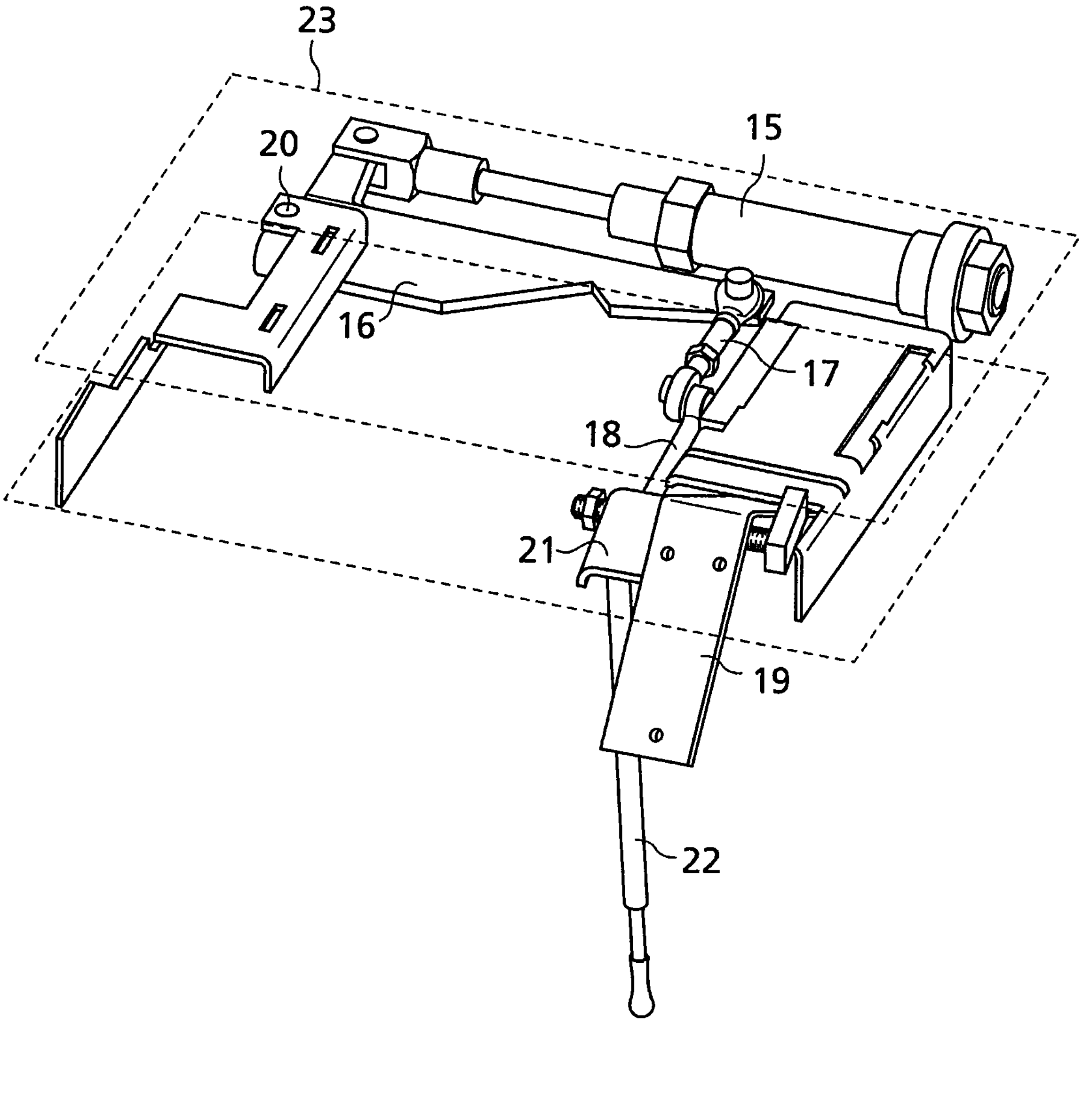
FIG. 3 shows a movement mechanism of a cover of a bank note processing machine.

FIG. 3 shows the structure of the movement mechanism for opening and closing the covers 6. In FIG. 3 there is represented the mechanism for a small cover 6 and therefore comprises only one actuating cylinder 15.

Larger covers 6, because of their greater weight, however, require two or more actuating cylinders. The second actuating cylinder then is disposed for example mirror-symmetrically next to the first actuating cylinder and acts via corresponding mechanical components upon a second suspension of the cover. The larger covers 6 with two actuating cylinders are usually used with the input module and the stacking module. The other modules require, due to their smaller size, usually only one actuating cylinder 15. The actuating cylinder 15 is formed as a pneumatic cylinder here.

Very small covers, as they can be present for example at the operating module, may not have a drive on their own in the form of an actuating cylinder 15, but are moved along with an adjacent cover 6.

As to not hinder the access of the operator to the interior of the modules, the actuating cylinders 15 and further mechanical components necessary for the movement of the respective covers 6 are accommodated in each case in the machine frame 23 of the bank note processing machine 1, cf. the area outlined in dashed lines in FIG. 3. In FIG. 1 there is shown by way of example the section of the machine frame 23, in which are disposed the actuating cylinder 15 and the further mechanical components for opening the cover 6 of the output module 4 (for this, the upper right part of the cover 6 of the output module 4 is shown broken out).

The actuating cylinder 15 is connected with a deflection member 16 which also functions as step-up or step-down. The deflection member 16 is rotatably mounted in a pivotal point 20 in a fixed part of the machine frame 23 of the bank note processing machine and thus transmits the movement of the actuating cylinder 15 to a coupling member 17. This can be adjusted in its length, in order to determine the end points of the movement and to make possible a complete opening and closing of the respective cover 6. The coupling member 17 guides a push rod 18 which is connected with the suspension 19 of the cover 6 and moves the cover. The cover 6 (not shown) is fastened to the suspension 19 and is opened or closed by the transmitted movement. The angle 21 upon which the push rod 18 acts is designed such that also a gas pressure spring 22 can act upon it, which supports the movements of the cover 6 and serves to hold open the cover 6.

In the represented structure, present components, such as hinges or suspensions, can remain almost unchanged. Only an additional point of action for the push rod 18 is required, in order to transmit the movement of the actuating cylinder 15 to the cover 6.

The invention claimed is:

1. An apparatus for processing documents of value comprising:

several processing zones located on the apparatus and arranged to process documents of value, each of said several processing zones having at least one door moveable between an open and a closed position, said apparatus comprising sensors arranged to detect events which require an intervention of an operator of the apparatus;

a control unit; and at least one actuator associated with each door of the several processing zones arranged to open the door under the control of the control unit, wherein said control unit is arranged to monitor the sensors and as soon as the respective sensor detects a malfunction to select a correct door out of the several doors of the several processing zones associated with the event detected by the respective sensor; and to automatically operate the at least one actuator of a respective door upon detection of an event associated with the respective processing zone at which the door is located, so that by the selected correct door opening automatically an operator is led directly to the one processing zone of the several processing zones in which the intervention of the operator is required, wherein the apparatus is arranged to indicate the automatic opening of the door by one or more acoustic and/or visual signals before the automatic opening of the correct door.

2. The apparatus according to claim 1, wherein the event is the malfunction whose elimination requires an intervention of the operator, includes at least one of: a malfunction of a strapping device, of a bundling device, of one of the sensors, of a light barrier or a transport malfunction, or the finding of a need for consumables of the apparatus.

3. The apparatus according to claim 2, wherein the event is a transport malfunction and the transport malfunction is a bank note jam.

4. The apparatus according to claim 1, wherein the door is closeable automatically.

5. The apparatus according to claim 4, wherein said door is configured to be closed automatically when a switch is activated by the operator and/or when the apparatus has detected a certain event which was triggered through the intervention of the operator.

6. The apparatus according to claim 1, comprising sensors arranged to detect the completely opened and completely closed position of the door.

7. The apparatus according to claim 1, wherein the apparatus can be configured such that the automatic opening of the door is effected only after an opening confirmation by the operator of the apparatus.

8. The apparatus according to claim 1, wherein said at least one actuator comprises an actuating cylinder connected to the door.

9. The apparatus according to claim 8, further comprising a valve connected with the actuating cylinder, said valve being arranged to slow down an opening movement of the door or a closing movement of the door by a temporary at least partial closure of the valve.

10. The apparatus according to claim 1, wherein the several processing zones are different processing zones from one another.

11. The apparatus according to claim 8, comprising, in addition to the at least one actuator for each at least one door, at least one gas pressure spring for each at least one door, said at least one gas pressure spring configured to support the opening movement of the door and to hold the door in fully opened position after its opening.

12. The apparatus according to claim 1, wherein the apparatus for processing documents is configured to stop when the correct door is opened, and configured to continue operation when all of the doors are closed.

13. A method for operating an apparatus for processing documents of value, said apparatus having several processing zones each having at least one door moveable between an open and a closed position, said method comprising the steps:

detecting events requiring an intervention of an operator in the processing zones using sensors, wherein said events require an intervention of an operator; and as soon as a respective sensor detects a malfunction in one of the processing zones, using a control unit to select a correct door out of several doors of the several processing zones associated with the event detected by the respective sensor, and to automatically operate at least one actuator associated with the door of the processing zone upon detection of the event associated with the respective processing zone at which the door is located so that by the selected correct door opening automatically an operator is led directly to the one processing zone of the several processing zones in which the intervention of the operator is required, wherein the selected correct door opening automatically is indicated by one or more acoustic and/or visual signals before the automatic opening.

14. The method according to claim 13, further comprising the steps of assisting in the opening movement of the respective door using one gas pressure spring per door, and after the opening holding the door in fully opened position by the gas pressure spring.

15. The method according to claim 13, comprising the step of automatically closing the door by activating a switch and/or when the apparatus has detected an event which was triggered through the intervention of the operator.

16. The method according to claim 13, including the step of detecting the completely opened and/or the completely closed position of the door.

17. The method according to claim 13, further comprising the step of temporarily closing a valve connected with the actuator so that a closing movement of the door from an open position or an opening movement of the door from a closed position is slowed down, wherein the actuator is a fluid actuator.

18. The method according to claim 13, wherein the actuator is a fluid cylinder.

19. An apparatus for processing documents of value comprising:

several processing zones located on the apparatus and arranged to process documents of value, each of said several processing zones having at least one door moveable between an open and a closed position, said apparatus comprising sensors arranged to detect events which require an intervention of an operator of the apparatus;

a control unit; and at least one actuator associated with each door of the several processing zones arranged to open the door under the control of the control unit, wherein said control unit is arranged to monitor the sensors and as soon as the respective sensor detects a malfunction to select a correct door out of the several doors of the several processing zones associated with the event detected by the respective sensor; and to automatically operate the at least one actuator of a respective door upon detection of an event associated with the respective processing zone at which the door is located, so that by the selected correct door opening automatically an operator is led directly to the one processing zone of the several processing zones in which the intervention of the operator is required, and wherein the apparatus is arranged to indicate the automatic opening of the door by one or more acoustic and/or visual signals before the automatic opening of the door.

20. A method of notifying an operator of a bank note processing machine with multiple processing zones, said method comprising the following steps:

detecting a first event which requires an intervention by the operator using sensors;

determining a first processing zone of the machine out of the multiple processing zones which is associated with the detected first event; and wherein as soon as the detected first event is detected, automatically selecting a correct door out of multiple doors of the multiple processing zones so that by the selected correct door opening automatically the operator is notified and led directly to the first processing zone in which the intervention is required, wherein the selected correct door opening automatically is indicated by one or more acoustic and/or visual signals before the automatic opening.

* * * * *